(12) United States Patent
Colling et al.

(10) Patent No.: US 6,986,802 B2
(45) Date of Patent: Jan. 17, 2006

(54) SELECTIVE SEPARATION OF FLUID COMPOUNDS UTILIZING A MEMBRANE SEPARATION PROCESS

(75) Inventors: Craig W. Colling, Warrenville, IL (US); Bo Chen, Aurora, IL (US); George A. Huff, Jr., Naperville, IL (US)

(73) Assignee: BP Corporation North America Inc., Warrenville, IL (US)

( * ) Notice: Subject to any disclaimer, the term of this patent is extended or adjusted under 35 U.S.C. 154(b) by 195 days.

(21) Appl. No.: 10/650,645

(22) Filed: Aug. 28, 2003

(65) Prior Publication Data

US 2005/0045029 A1 Mar. 3, 2005

(51) Int. Cl.
*B01D 53/22* (2006.01)

(52) U.S. Cl. .......................... 95/46; 95/50; 96/6; 96/8; 96/9; 96/14; 210/637; 210/640; 585/805; 585/818

(58) Field of Classification Search ............. 95/45–56; 96/4, 6–9, 12–14; 210/637, 640; 585/805, 585/818, 819
See application file for complete search history.

(56) References Cited

U.S. PATENT DOCUMENTS

| | | | | |
|---|---|---|---|---|
| 2,960,462 A | * | 11/1960 | Jennings et al. ............. 208/308 |
| 2,985,588 A | * | 5/1961 | Binning et al. ............. 585/819 |
| 3,244,763 A | * | 4/1966 | Cahn ........................... 585/818 |
| 3,299,157 A | * | 1/1967 | Baddour et al. ............ 585/819 |
| 3,504,048 A | * | 3/1970 | Rosset ........................ 585/819 |
| 3,536,611 A | * | 10/1970 | Filippi et al. ............... 210/646 |
| 4,894,068 A | * | 1/1990 | Rice ................................ 95/51 |
| 4,925,562 A | * | 5/1990 | te Hennepe et al. .... 210/500.25 |
| 4,962,270 A | * | 10/1990 | Feimer et al. ............... 585/819 |
| 5,107,059 A | * | 4/1992 | Chen et al. ................. 585/818 |
| 5,169,530 A | * | 12/1992 | Schucker et al. ............. 239/88 |
| 5,282,969 A | * | 2/1994 | Xu ............................... 210/640 |
| 5,352,361 A | * | 10/1994 | Prasad et al. .......... 210/321.81 |
| 5,396,019 A | * | 3/1995 | Sartori et al. ................ 585/819 |
| 5,427,687 A | | 6/1995 | Blum et al. .................. 210/638 |
| 5,463,121 A | | 10/1995 | Sridhar ........................ 562/600 |
| 5,464,540 A | * | 11/1995 | Friesen et al. .............. 210/640 |
| 5,470,469 A | * | 11/1995 | Eckman .................... 210/321.8 |
| 5,494,556 A | * | 2/1996 | Mita et al. ....................... 203/2 |
| 5,505,855 A | * | 4/1996 | Haussmann ................. 210/652 |
| 5,512,179 A | | 4/1996 | Brüschke et al. ........... 210/640 |
| 5,611,842 A | * | 3/1997 | Friesen et al. ................. 95/50 |
| 5,616,247 A | * | 4/1997 | Mita et al. ................... 210/640 |
| 5,843,209 A | * | 12/1998 | Ray et al. ....................... 95/52 |
| 5,858,066 A | * | 1/1999 | O'Brien et al. ................. 95/48 |
| 5,863,420 A | * | 1/1999 | Kwasniewski et al. ..... 208/308 |
| 5,873,928 A | * | 2/1999 | Callahan ......................... 95/45 |
| 6,187,987 B1 | * | 2/2001 | Chin et al. .................. 585/819 |

(Continued)

FOREIGN PATENT DOCUMENTS

EP 0457981 A1 * 11/1991

(Continued)

*Primary Examiner*—Robert H. Spitzer
(74) *Attorney, Agent, or Firm*—Thomas A. Yassen (57) ABSTRACT

Apparatus and processes are disclosed for economical separation of fluid mixtures utilizing perm-selective membranes. Broadly, apparatus of the invention comprises a plurality of membrane modules comprising a solid perm-selective membrane and equipment for controlling enthalpy of selected fluids within the apparatus. Advantageously, the membrane modules are disposed in a first product group, a second product group, and at least one intermediate group. Apparatus of the invention is particularly useful for simultaneous recovery of a very pure permeate product, and/or a desired non-permeate stream, from fluid mixtures of two or more compounds which when subjected to appropriately altered conditions of temperature and/or pressure exhibit a bubble point.

20 Claims, 1 Drawing Sheet

U.S. PATENT DOCUMENTS

| | | | |
|---|---|---|---|
| 6,376,733 B1 * | 4/2002 | Ferraro et al. | 585/805 |
| 6,387,157 B1 * | 5/2002 | Yamashita | 95/45 |
| 6,592,749 B1 * | 7/2003 | Lokhandwala et al. | 208/102 |
| 2002/0045792 A1 * | 4/2002 | Takahashi et al. | 585/819 |
| 2002/0082462 A1 * | 6/2002 | Ferraro et al. | 585/818 |

FOREIGN PATENT DOCUMENTS

| | | |
|---|---|---|
| EP | 0701856 A1 * | 3/1996 |
| GB | 1222101 | 2/1968 |
| JP | 1155928 | 6/1989 |

* cited by examiner

SELECTIVE SEPARATION OF FLUID COMPOUNDS UTILIZING A MEMBRANE SEPARATION PROCESS

TECHNICAL FIELD

The present invention relates to processes for recovery of purified products from a fluid mixture by means of permselective membrane separation apparatus. More particularly, the integrated apparatus of the invention comprises a plurality of membrane modules comprising a solid permselective membrane and means for controlling enthalpy of selected fluids within the apparatus. Apparatus of the invention is particularly useful for simultaneous recovery of a very pure permeate product, and/or a desired non-permeate stream, from a fluid mixture of two or more compounds which when subjected to appropriately altered conditions of temperature and/or pressure exhibit a bubble point.

BACKGROUND OF THE INVENTION

Membrane processes useful for the separation of gaseous mixtures employ large differentials in chemical potential, usually applied as a pressure gradient, across a membrane to drive separations. On the permeate side of the membrane, low pressure is usually maintained by the use of compressors, vacuum pumps, or low temperature condensers. On the feed side of the membrane, the driving force is kept high by using high pressure or high temperature.

Membranes useful for the separation of gaseous mixtures are of two very different types: one is microporous while the other is nonporous. Discovery of the basic laws governing the selectivity for gases effusing through a microporous membrane is credited to T. Graham. When the pore size of a microporous membrane is small compared to the mean-free-path of non-condensable gas molecules in the mixture, the permeate is enriched in the gas of the lower molecular weight. Practical and theoretical enrichments achievable by this technique are very small because the molecular weight ratios of most gases are not very large and the concomitant selectivities are proportional to the square roots of these ratios. Therefore, a large number of separation stages is needed to effect an efficient separation of a given gas from a gaseous mixture. However, because this method of separation relies solely on mass ratios and not chemical differences among the effusing species, it is the only membrane based method capable of separating isotopes of a given element. For this reason, this method was chosen to enrich uranium in the fissionable isotope 235 for development of the atomic bomb during World War II. However, this method of separation is inherently expensive due to the large amount of capital investment needed for processing a necessary large amount of gas, stringent membrane specifications requiring high porosity and small pore size, and high energy requirements for operation.

In nonporous membrane systems, molecules permeate through the membrane. During permeation across the nonporous membrane, different molecules are separated due to the differences of their diffusivity and solubility within the membrane matrix. Not only does molecular size influence the transport rate of each species through the matrix but also the chemical nature of both the permeating molecules and the polymer matrix itself. Thus, conceptually useful separations should be attainable.

Vapor permeation is very closely related to membrane gas separation, as pointed out by Gas separation is one of the largest applications of membrane technology. For example, see Lee and Koros in "Membranes, Synthetic, Applications" published in the Encyclopedia of Physical Science and Technology, Third Edition, Volume 9, Academic Press (2002).

Membrane based technology for the production of nitrogen from air, removal of carbon dioxide from natural gas, and purification of hydrogen occupy significant shares of the markets for these processes. Most of the technical challenge for membranes for these applications has been in developing membrane materials that can selectively remove the desired component. A number of patents that have been issued for specific membrane materials, however little attention has been given to the heat balance around the membrane apparatus, primarily because components previously considered for membrane based separations (nitrogen, oxygen, carbon dioxide, methane, hydrogen) are fixed gases. Such gases do not exist both as a liquid and a vapor at typical conditions of industrial process.

The art is replete with processes said to fabricate membranes possessing both high selectivity and high fluxes. Without sufficiently high fluxes the required membrane areas required would be so large as to make the technique uneconomical. It is now well known that numerous polymers are much more permeable to polar gases (examples include $H_2O$, $CO_2$, $H_2S$, and $SO_2$) than to nonpolar gases ($N_2$, $O_2$, and $CH_4$), and that gases of small molecular size (He, $H_2$) permeate more readily through polymers than large molecules ($CH_4$, $C_2H_4$).

Pervaporation refers to a membrane process where the feed to the membrane is a liquid. High driving force is maintained by warming the liquid and keeping the permeate at low pressure. As material passes across the membrane, energy is transferred from the feed to the permeate. This loss of energy from the feed side tends to cool the feed and lower the membrane driving force. In order to reestablish a high driving force, the liquid must be reheated. In practice, this leads to staged membranes with interstage reheating. However, Rautenbach and Albrecht state in an article entitled "The Separation Potential of Pervaporation, Part 2: Process Design and Economics" published in Journal of Membrane Science, vol. 25, pp. 25–54 (1985) that the complexity of multi-stage pervaporation processes would make commercial application unfavorable.

There do appear to be cases where pervaporation is efficient enough to be practiced on an industrial scale. Baker states in a book entitled "Membrane Technology and Applications" published by McGraw-Hill (2000) that one of the largest applications of pervaporation is the dehydration of ethanol. Hendrikus et al. describe in U.S. Pat. No. 4,925,562 a pervaporation membrane useful for the permeation of several alcohols. Shucker et al. describe a multistage pervaporation process in European Patent Application Publication Number 0457981 A1. Pervaporation also appears attractive when employed in concert with other separation technologies. A review article entitled "Pervaporation-based hybrid process: a review of process design, applications, and economics" published by Lipnizki et al. in Journal of Membrane Science, vol. 153, pp. 183–22 (1999) examined several pervaporation membrane hybrids.

One way to keep the driving force high on the feed side of the membrane is to increase the energy of the feed stream so that energy losses due to permeation are not as significant. Adding energy to the feed so as to vaporize the feed results in a process called vapor permeation. There are very few descriptions of vapor permeation in the prior art. Friesen et al. describe a process useful to separate mixtures of vapors in European Patent Application Publication EP0701856A1.

For polymeric membranes, a large pressure gradient across the membrane would supply the driving force for permeation. This driving force would induce a cooling in the membrane (for materials with positive Joule-Thomson coefficients) in order to produce the low pressure permeate. This affect is not present in facilitated transport membranes and has not been incorporated in previous processes based on them. Most of this work focused on details of the internals of the facilitated transport membrane device and not on how to incorporate them into a process that produced products that met market specifications.

Some of the most difficult separations in the petrochemical industry involve the separation of one isomer of an aromatic compound from another and/or other organic compounds, for example isomers of xylene and ethylbenzene. The separation and purification of para-xylene (PX) from mixed xylenes is an energy and capital intensive process. Industrial processes used today employ energy-intensive cryogenic separations or capital-intensive absorbent technology to produce high purity PX. It is widely recognized that, next to feedstock costs, the purification section is the most expensive part of the para-xylene production.

There is, therefore, a present need for processes and apparatus using perm-selective membranes to provide heat integrated membrane apparatus where pressure-driven (fugacity-driven) membranes for the separation of selected compounds from mixtures which when subjected to appropriately altered process conditions of temperature and/or pressure exhibit a bubble point. Advantageously, a new process should overcome the recovery limitation imposed by membrane cooling encountered in pervaporation.

Improved apparatus should provide for an integrated sequence, carried out with streams in gas and/or liquid state, using a suitable perm-selective membrane, preferably a solid perm-selective membrane which under a suitable differential of a driving force exhibits selective permeability of a desired product, i.e., incorporate pressure-driven (fugacity-driven) membranes with existing separation assets.

SUMMARY OF THE INVENTION

In broad aspect, the present invention is directed to integrated membrane separation apparatus and uses thereof for economical separation of fluid mixtures. More particularly, apparatus of the invention comprises a plurality of membrane modules comprising a solid perm-selective membrane and means for controlling enthalpy of selected fluids within the apparatus. Apparatus of the invention is particularly useful for simultaneous recovery of a very pure permeate product, and/or a desired non-permeate stream, from fluid mixtures of two or more compounds which when subjected to appropriately altered conditions of temperature and/or pressure exhibit a bubble point.

Advantageously, the membrane modules are disposed in a first product group, a second product group, and at least one intermediate group. Each module includes first and second zones separated by a solid perm-selective membrane which under a suitable differential of a driving force exhibits a permeability of at least 0.1 Barrer for one of the compounds of the feedstock. Each first zone has at least one inlet and outlet for flow of fluid in contact with the membrane, and contiguous with the opposite side thereof a second zone having at least one outlet for flow of permeate. Beneficially apparatus of the invention is employed for simultaneous recovery of a very pure permeate product and another desired product from a mixture containing organic compounds.

In one aspect this invention provides a process using perm-selective membranes for simultaneous recovery of a permeate product and a desired non-permeate product from a fluid mixture of compounds, which process comprises: (a) providing a feedstream comprising a mixture of two or more compounds which when subjected to appropriately altered conditions of temperature and/or pressure exhibit a bubble point; (b) providing apparatus comprising means for controlling enthalpy of selected fluids within the apparatus and one or more membrane modules each including first and second zones separated by a solid perm-selective membrane which under a suitable differential of a driving force exhibits a permeability of at least 0.1 Barrer for one of the compounds of the feedstock, each first zone having at least one inlet and outlet for flow of fluid in contact with the membrane, and contiguous with the opposite side thereof a second zone having at least one outlet for flow of permeate; (c) introducing the feedstream into the first zone of one or more of the modules under conditions suitable for permeation, and thereby obtaining permeate and non-permeate streams from the modules; and (d) controlling enthalpy to maintain the Membrane Efficiency Index of the non-permeate fluid within a range from about 0.5 to about 1.5.

For the purposes of the present invention, "Membrane Efficiency Index" (MEI) is defined as a ratio of the difference between the specific enthalpy of the feed stream entering the membrane device and specific enthalpy of the nonpermeate fluid effluent to the difference between the specific enthalpy of the feed stream and the bubble point specific enthalpy of the nonpermeate fluid at the nonpermeate product pressure and composition.

In another aspect this invention provides a process using perm-selective membranes in multiple groups for simultaneous recovery of desired non-permeate product and purified permeate product from fluid mixtures, which process comprises: (i) providing a feedstream comprising a mixture of two or more compounds which when subjected to appropriately altered conditions of temperature and/or pressure exhibit a bubble point; (ii) providing apparatus comprising means for controlling enthalpy of selected fluids within the apparatus and a plurality of membrane modules disposed in a first product group, a second product group, and at least one intermediate group, each module including first and second zones separated by a solid perm-selective membrane which under a suitable differential of a driving force exhibits a permeability of at least 0.1 Barrer for one of the compounds of the feedstock, each first zone having at least one inlet and outlet for flow of fluid in contact with the membrane, and contiguous with the opposite side thereof a second zone having at least one outlet for flow of permeate; (iii) introducing the feedstream into the first zone of one or more of the first product modules under conditions suitable for permeation, and thereby obtaining permeate and non-permeate product streams from the first product modules; (iv) distributing the permeate from the first product modules into the first zone of one or more of the intermediate modules under conditions suitable for permeation, and thereby obtaining permeate and non-permeate streams from the intermediate modules; (v) returning at least a portion of the non-permeate from the intermediate modules into the first zone of one or more of the first product modules under conditions suitable for permeation; (vi) distributing the permeate from the second zones of the intermediate group of modules into the first zones of the second product group modules under conditions suitable for permeation, thereby obtaining non-permeate streams and final permeate product streams from the second product modules; (vii) returning at least a portion of the non-permeate from the second product modules into the first zone of one or more of the intermediate modules under conditions suitable for permeation; and (viii) controlling enthalpy to maintain the Membrane Efficiency Index of at least one non-permeate fluid within a range from about 0.5 to about 1.5.

In one aspect, the invention provides integrated separation apparatus wherein the Membrane Efficiency Index of the non-permeate fluid from at least the second product modules is maintained within a range from about 0.5 to about 1.5. Beneficially, the Membrane Efficiency Index of the non-permeate fluid from the second product modules and the intermediate modules and/or the first product modules are maintained within a range from about 0.5 to about 1.5.

This invention contemplates the treatment of a fluid feedstock, e.g. various type organic materials, especially a fluid mixture of compounds of petroleum origin. In general, the fluid feedstock is a gaseous mixture comprising a more selectively permeable component and a less permeable component. Advantageously one or more of the module inlet streams may comprises a mixture of liquid and condensable vapor. Optionally, the apparatus may further comprise means for distribution of a "sweep" stream into the permeate chambers, but typically no sweep is required.

Apparatus of the invention are particularly useful in processes for treatment of a gaseous mixture comprised of a more selectively permeable isomer of an aromatic compound, for example at least one isomer of xylene and/or ethylbenzene.

In yet another aspect, the invention provides integrated separation apparatus using perm-selective membranes in multiple groups for simultaneous recovery of desired non-permeate product and purified permeate product from fluid mixtures, which apparatus comprises: a plurality of membrane modules disposed in a first product group, a second product group, and at least one intermediate group, each module including first and second zones separated by a solid perm-selective membrane which under a suitable differential of a driving force exhibits a permeability of at least 0.1 Barrer for one of the compounds of the feedstock, each first zone having at least one inlet and outlet for flow of fluid in contact with the membrane, and contiguous with the opposite side thereof a second zone having at least one outlet for flow of permeate; means for distributing permeate from the first product modules into the first zone of one or more of the intermediate modules under conditions suitable for permeation, and returning non-permeate streams from the intermediate modules to inlets of the first product modules; means for distributing permeate from the intermediate modules into the first zone of one or more of the second product modules under conditions suitable for permeation, and returning non-permeate streams from the second product modules to inlets of the intermediate modules; and means for controlling enthalpy of selected fluids within the apparatus to maintain the Membrane Efficiency Index of at least one non-permeate fluid within a range from about 0.5 to about 1.5.

This invention is particularly useful towards separations involving organic compounds, in particular compounds which are difficult to separate by conventional means such as fractional crystallization. Typically, these include organic compounds that are chemically related as for example a process for the separation and purification of para-xylene from mixed xylenes. Compared to current technologies for para-xylene purification, para-xylene is produced from the membrane process described herein at significantly reduced capital, operating, and energy costs. The invention can also simultaneously meet para-xylene purity requirements and recover more para-xylene than conventional para-xylene purification processes. Having similar boiling points, simple distillation is a cost prohibitive method of purifying para-xylene from C8 aromatics.

For a more complete understanding of the present invention, reference should now be made to the embodiments illustrated in greater detail in the accompanying drawing and described below by way of examples of the invention.

BRIEF DESCRIPTION OF THE DRAWING

The invention is hereinafter described in detail with reference to the accompanying drawing which is a schematic flow diagram depicting aspects of the membrane separation processes and apparatus of the present invention for simultaneous recover of a very pure permeate products and one or more desired non-permeate product. The drawing depicts an embodiment of the present invention in which a plurality of membrane separation devices is used to modify the composition of a mixture of chemical compounds.

GENERAL DESCRIPTION

Any solid perm-selective membrane which under a suitable differential of a driving force exhibits a permeability and other characteristics suitable for the desired separations may be used according to the invention. Suitable membranes may take the form of a homogeneous membrane, a composite membrane or an asymmetric membrane which, for example may incorporate a gel, a solid, or a liquid layer. Widely used polymers include silicone and natural rubbers, cellulose acetate, polysulfones and polyimides.

Preferred membranes for use in vapor separation embodiments of the invention are generally of two types. The first is a composite membrane comprising a microporous support, onto which the perm-selective layer is deposited as an ultra-thin coating. Composite membranes are preferred when a rubbery polymer is used as the perm-selective material. The second is an asymmetric membrane in which the thin, dense skin of the asymmetric membrane is the perm-selective layer. Both composite and asymmetric membranes are known in the art. The form in which the membranes are used in the invention is not critical. They may be used, for example, as flat sheets or discs, coated hollow fibers, spiral-wound modules, or any other convenient form.

The driving forces for separation of vapor components by membrane permeation include, predominately their partial pressure difference between the first and second sides of the membrane. The pressure drop across the membrane can be achieved by pressurizing the first zone, by evacuating the second zone, introducing a sweep stream, or any combination thereof.

The membranes used in each group of modules may be of the same type or different. Although both units may contain membranes selective to the desired component to be separated, the selectivities of the membranes may be different. For example, where intermediate modules process the bulk of the fluid feedstock, these modules may contain membranes of high flux and moderate selectivity. The module group which deals with smaller streams, may contain membranes of high selectivity but lower flux. Likewise the intermediate modules may contain one type of membrane, and product modules may contain another type, or all three groups may contain different types. Useful embodiments are also possible using membranes of unlike selectivities in the intermediate modules and product modules.

Suitable types of membrane modules include the hollow-fine fibers, capillary fibers, spiral-wound, plate-and-frame, and tubular types. The choice of the most suitable membrane module type for a particular membrane separation must balance a number of factors. The principal module design parameters that enter into the decision are limitation to specific types of membrane material, suitability for high-pressure operation, permeate-side pressure drop, concentration polarization fouling control, permeability of an optional sweep stream, and last but not least costs of manufacture.

Hollow-fiber membrane modules are used in two basic geometries. One type is the shell-side feed design, which has been used in hydrogen separation systems and in reverse osmosis systems. In such a module, a loop or a closed bundle of fibers is contained in a pressure vessel. The system is pressurized from the shell side; permeate passes through the fiber wall and exits through the open fiber ends. This design is easy to make and allows very large membrane areas to be contained in an economical system. Because the fiber wall must support considerable hydrostatic pressure, the fibers usually have small diameters and thick walls, e.g. 100 mm to 200 mm outer diameter, and typically an inner diameter of about one-half the outer diameter.

A second type of hollow-fiber module is the bore-side feed type. The fibers in this type of unit are open at both ends, and the feed fluid is circulated through the bore of the fibers. To minimize pressure drop inside the fibers, the diameters are usually larger than those of the fine fibers used in the shell-side feed system and are generally made by solution spinning. These so-called capillary fibers are used in ultra-filtration, pervaporation, and some low- to medium-pressure gas applications.

Concentration polarization is well controlled in bore-side feed modules. The feed solution passes directly across the active surface of the membrane, and no stagnant dead spaces are produced. This is far from the case in shell-side feed modules in which flow channeling and stagnant areas between fibers, which cause significant concentration polarization problems, are difficult to avoid. Any suspended particulate matter in the feed solution is easily trapped in these stagnant areas, leading to irreversible fouling of the membrane. Baffles to direct the feed flow have been tried, but are not widely used. A more common method of minimizing concentration polarization is to direct the feed flow normal to the direction of the hollow fibers. This produces a cross-flow module with relatively good flow distribution across the fiber surface. Several membrane modules may be connected in series, so high feed solution velocities can be used. A number of variants on this basic design have been described, for example U.S. Pat. No. 3,536,611 in the name of Fillip et al., U.S. Pat. No. 5,169,530 in the name of Sticker et al., U.S. Pat. No. 5,352,361 in the name of Prased et al., and U.S. Pat. No. 5,470,469 in the name of Beckman which are incorporated herein by reference each in its entirety. The greatest single advantage of hollow-fiber modules is the ability to pack a very large membrane area into a single module.

DESCRIPTION OF THE PREFERRED EMBODIMENTS

Para-xylene is produced or separated from petroleum and chemical feedstocks as a commodity chemical ultimately used in the production of polyester fiber and resin. When removed from most petroleum-derived feedstocks, para-xylene is found in mixtures with other C8 aromatics; namely: meta-xylene (mX), ortho-xylene (oX), and ethyl-benzene (EB). The three xylene isomers have an equilibrium ratio of approximately 1:2:1 for PX:mX:oX, and depending on the source, ethylbenzene can comprise up to about 20 percent by weight of a C8 aromatics mixture leaving a balance typically of from about 80 to about 99 percent by weight of xylene. Beneficially processes of this invention efficiently recovery purified para-xylene from the near equilibrium mixture, and submitting the remainder of the stream to an isomerization reactor to re-establish the equilibrium.

Figure 1:
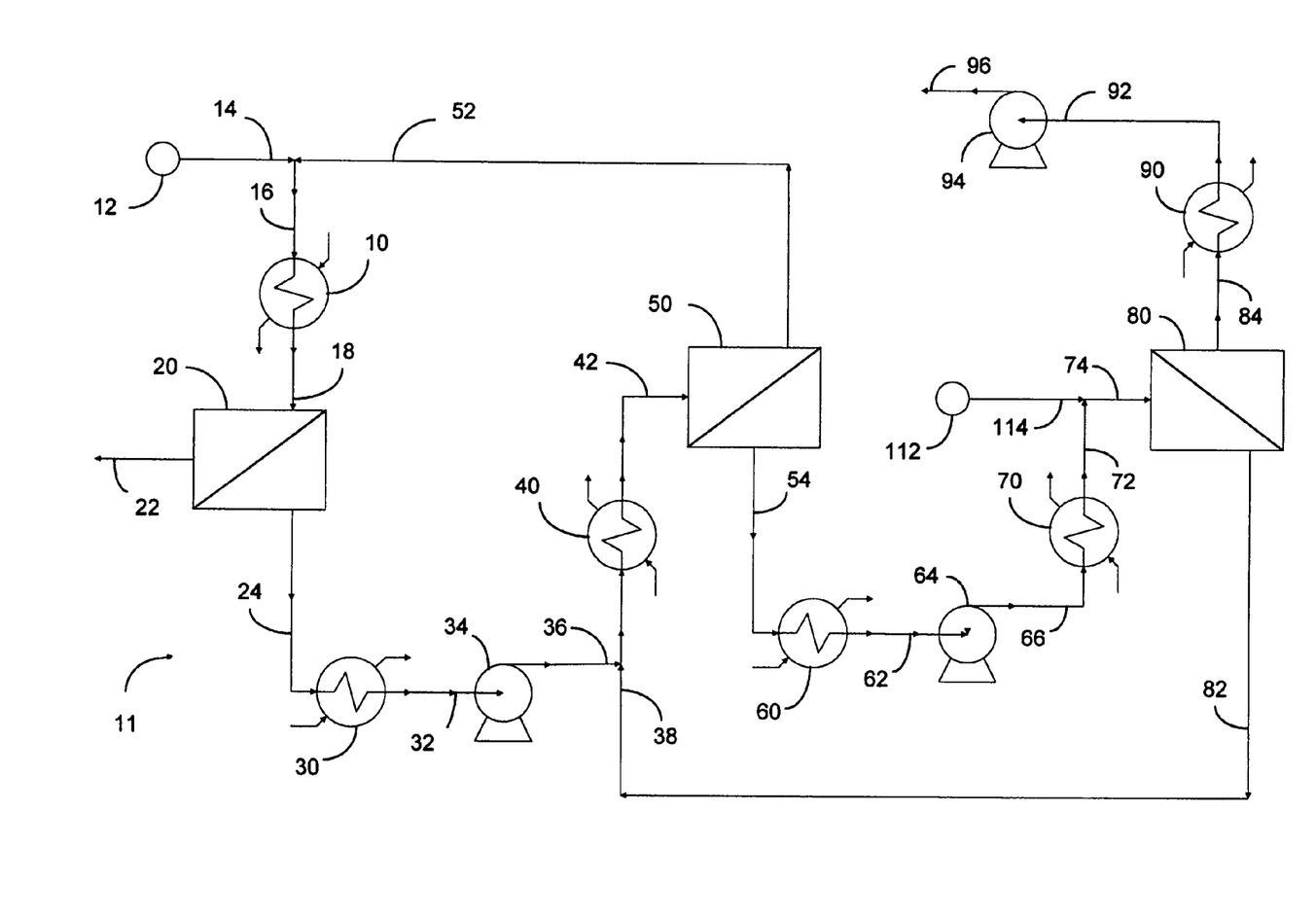

Referring to the right side of the drawing, where a membrane device 20 is disposed according to a preferred aspect of the invention. Membrane device 20 comprises a perm-selective membrane that under suitable differential of driving force exhibits a permeability of at least 0.01 Barrer, channels having at least one inlet and one outlet for flow of fluid in contact with one side of a membrane, and contiguous with the opposite side thereof a permeate chamber having at least one outlet for flow of permeate. A mixture of two or more compounds which when subjected to appropriately altered conditions of temperature and/or pressure exhibit a bubble point is introduced through conduit 18. The enthalpy of the feed is adjusted by suitable means, for example of exchanger 10 such that the Membrane Efficiency Index of the nonpermeate fluid, withdrawn through conduit 22, is within a range from about 0.5 to about 1.5. Permeate is withdrawn through conduit 24.

For many industrial uses the permselectivity of available membrane devices is insufficient to meet the required product purity and/or product recovery. In such cases, a process using perm-selective membranes in multiple groups is necessary for simultaneous recovery of desired non-permeate product and purified permeate product from fluid mixtures. For example in accordance with the invention, a plurality of membrane modules disposed in two or more groups, for example, a first product group and a second product group, and optionally one or more intermediate groups.

In the apparatus depicted in the drawing, membrane modules 20, 50 and 80 are disposed according to one aspect of the invention. A suitable mixture to be separated is supplied from source 12 to exchanger 10 through conduit 14 and manifold 16. The admixture which includes nonpermeate from module 50 is introduced via inlets into membrane module 20 through conduit 18. Nonpermeate product is transferred from membrane module 20 to storage (not shown) through conduit 22. Permeate is withdrawn from membrane module 20 through conduit 24 and exchanger 30. Heat exchanger 30 is operated at low temperatures that produce pressures low enough to generate an adequate driving force for permeation in membrane module 20.

Pump 34 is used to pressurize fluid withdrawn from exchanger 30 through conduit 32, and transfer the stream into manifold 38 through conduit 36. In other embodiments of the invention all or a portion of a mixture to be separated is introduced through manifold 38. The mixed stream which includes nonpermeate from module 80 is introduced via inlets to membrane module 50 through exchanger 40 and conduit 42. Nonpermeate product is transferred from membrane module 50 into manifold 16 through conduit 52. Permeate is withdrawn from membrane module 50 through conduit 54 and exchanger 60. Heat exchanger 60 is operated at low temperatures that produce pressures low enough to generate an adequate driving force for permeation in membrane module 50.

Pump 64 is used to pressurize fluid withdrawn from exchanger 60 through conduit 62, and transfer the stream through conduit 66, exchanger 70, and into manifold 74 through conduit 72. In other embodiments of the invention all or a portion of a mixture to be separated is supplied from source 112 through conduit 114 and introduced through manifold 74. Nonpermeate from module 80 is returned to membrane module 50 through conduit 82 and manifold 38. Permeate is withdrawn from membrane module 80 through conduit 84 and exchanger 90. Heat exchanger 90 is operated at low temperatures that produce pressures low enough to generate an adequate driving force for permeation in membrane module 80. Pump 94 is used to pressurize fluid withdrawn from exchanger 90 through conduit 92, and transfer the purified product stream into storage (not shown) through conduit 96.

According to this embodiment of the invention, cooperation and interaction between aspects of perm-selective membrane separation modules beneficially operate to control enthalpy of the compressed effluent distributed into membrane device, thereby maintaining the Membrane Efficiency Index of the non-permeate fluid from membrane devices within a range from about 0.5 to about 1.5, preferably within a range from about 0.7 to about 1.1, and more preferably within a range from about 0.8 to about 1.05.

In preferred embodiments of the present invention, pumps 34 and 64, heat exchangers 10, 40 and 70, and the enthalpy of mixtures to be separated, for example from sources 12 and/or 112 are adjusted simultaneously so that the MEI of the nonpermeate product fluid from membrane module 20 is within a range from about 0.5 to about 1.5. In another embodiment of the present invention, pump 64, heat exchanger 70, and/or the enthalpy of a fluid mixture from source 112 are adjusted so that the MEI of the nonpermeate fluid from membrane module 80 is within a range from about 0.5 to about 1.5. In yet another embodiment of the present invention, pump 34, heat exchanger 40, and/or the enthalpy of a feed mixture are adjusted so that the MEI of the fluid in conduit 52 is within a range from about 0.5 to about 1.5; and heat exchanger 40 and/or the enthalpy of another feed mixture are adjusted so that the MEI of the nonpermeate fluid from membrane module 50 is within a range from about 0.5 to about 1.5.

EXAMPLES OF THE INVENTION

The following examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

General

These examples demonstrate beneficial aspects of processing configurations utilizing fugacity-driven membranes that are integrated with other processing steps for the separation and purification of para-xylene from mixtures of xylene isomers. In these examples, the results were obtained from computer calculations, performed using commercially available chemical process modeling programs (e.g. Aspen Plus from Aspen Technology, Inc.) where models of adiabatic membranes have been incorporated with standard chemical process equipment models. The models of membranes were developed by BP and based on generally accepted gas permeation equations. (See Shindo et al., "Calculation Methods for Multicomponent Gas Separation by Permeation," Sep. Sci. Technol. 20, 445–459 (1985), Kovvali et al., "Models and Analyses of Membrane Gas Permeators," J. Memb. Sci. 73, 1–23 (1992), and Coker et al., "Modeling Multicomponent Gas Separation Using Hollow-Fiber Membrane Contactors," AIChE J. 44, 1289–1302 (1998).)

Calculations were performed with a mixed xylene feed containing 7 percent ethylbenzene, 22 percent para-xylene, 50 percent meta-xylene, and 22 percent ortho-xylene. All the calculations were performed using a permeate condenser operating at 110° F. This was sufficient to generate a permeate pressure of approximately 25 Torr. The maximum operating temperature of the membranes was limited to be 300° F.

For the purposes of the present invention, the permeability of gases through membranes is measured in "Barrer", which is defined as $10^{-10}$ [$cm^3$ (STP) cm/($cm^2$·sec·cm Hg)] and named after R. M. Barrer. Membrane permeability is a measure of the ability of a membrane to permeate a gas. The term "membrane selectivity" is defined as the ratio of the permeabilities of two gases and is a measure of the ability of a membrane to separate the two gases. (For example, see Baker, Richard W., "Membrane Technology and Applications", pp. 290–291, McGraw-Hill, New York, 2000).

Example 1

The apparatus consisting of only module 20 as shown in the drawing was simulated using a para-xylene selectivity of 50 and para-xylene permeability of 5 Barrer. The fluid in conduit 18 was fed to the membrane module at 300° F. (at approximately 18 psia). The amount of area employed in membrane module 20 was varied and the feed pressure was adjusted at the same time so that the MEI was 1 for fluid in conduit 22. Results are shown in Table I.

TABLE I

Membrane Performance with MEI = 1.0

| Membrane Area ($\times 10^{-3}$ $ft^2$) | Permeate PX Content (percent by weight) | Permeate PX Recovery (percent by weight) | MEI | Membrane Feed Vapor Molar Fraction |
|---|---|---|---|---|
| 300 | 89 | 63 | 1.0 | 0.03 |
| 390 | 87 | 78 | 1.0 | 0.12 |
| 650 | 81 | 93 | 1.0 | 0.22 |

The results in Table I show that as permeate recovery increased permeate purity decreased. At the same time, more material passed through the membrane and membrane cooling increased as membrane area increased. As membrane cooling increased, it was necessary to further vaporize the feed in order to maintain a MEI of one.

This invention demonstrates the integration of pervaporation and vapor permeation, and shows that heating the feed so that it is partially vaporized or near its dew point keeps the driving force high and no limit in recovery is observed. It is more energy efficient than vapor permeation since it can meet the separation objectives without heating the feed as much.

At a MEI of one, the nonpermeate exited the membrane module as a liquid at its bubble point. If the nonpermeate needs to be pressurized (to be sent for further processing, storage, etc.), then it can be pumped without additional cooling. This is desirable because it leads to lower processing costs.

Example 2

This example documents effects of nonpermeate subcooling on membrane performance. Calculations were performed in this example with the same membrane areas employed in Example 1 while the membrane feed vapor fraction was maintained at 0.02. Para-xylene selectivity of 50, para-xylene permeability of 5 Barrer, and a 300° F. membrane feed temperature was again used.

In this example, the membrane is operating both in vapor permeation and pervaporation mode. Results shown in Table II indicate that as the membrane area increased subcooling of the nonpermeate also increased. Hence permeate recoveries were not as high as in Example 1 because membrane subcooling lowers the permeation driving force. This shows the advantages of operating the membrane so that significant subcooling does not occur.

TABLE II

Membrane Performance with Feed Vapor Fraction of 0.02

| Membrane Area ($\times 10^{-3}$ ft$^2$) | Permeate PX Content (percent by weight) | Permeate PX Recovery (percent by weight) | MEI | Nonpermeate Subcooling (° F.) |
|---|---|---|---|---|
| 300 | 89 | 61 | 1.1 | 3 |
| 390 | 88 | 67 | 1.8 | 24 |
| 650 | 86 | 77 | 4.2 | 50 |

Example 3

This example documents effects of heating the membrane feed so that the nonpermeate is a vapor-liquid mixture. Calculations were again performed with the same membrane areas employed in Example 1, but in this example the membrane feed vapor fraction was maintained at 0.3. Para-xylene selectivity of 50, para-xylene permeability of 5 Barrer, and 300° F. membrane feed temperature was again used.

Results of these calculations are shown in Table III. As membrane area increased, permeate recovery and membrane cooling increased. Consequently, the vapor content of the nonpermeate also decreased. If necessary, a cooler would need to be employed to completely condense the nonpermeate before it could be pressurized with a pump. However, this would lead to additional equipment and energy costs. The results shown in Table III show that the permeate recoveries in this example were better than Example 1 because the driving force was higher in this example.

TABLE III

Membrane Performance with Feed Vapor Fraction of 0.3

| Membrane Area ($\times 10^{-3}$ ft$^2$) | Permeate PX Content (percent by weight) | Permeate PX Recovery (percent by weight) | MEI | Nonpermeate Vapor Molar Fraction |
|---|---|---|---|---|
| 300 | 89 | 65 | 0.29 | 0.29 |
| 390 | 87 | 77 | 0.42 | 0.22 |
| 650 | 81 | 93 | 0.68 | 0.11 |

Example 4

Current commercial sources of fiber-grade para-xylene production are designed to meet a para-xylene product purity specification of 99.8 percent para-xylene. Units that purify para-xylene using crystallization technology have achieved a recovery of approximately 67 percent. Membrane-based processes for para-xylene purification must also meet these performance targets. It was necessary to increase the para-xylene selectivity to about 200 to meet these targets using the single membrane apparatus as in Example 1. Advantageously, these high performance targets are achieved by apparatus depicted in the drawing according to this invention.

Calculations were performed to simulate the use of the process shown in the drawing to produce a permeate product in conduit 96 that met the purity specification of 99.8 percent para-xylene and simultaneously matched the para-xylene recovery obtained in conventional crystallization processes of 67 percent. In this example, fresh mixed xylene feed was introduced only from source 12 via conduit 14. A para-xylene membrane selectivity of 15 and para-xylene permeability of 0.5 Barrer was employed in each membrane module.

The amount of membrane area in device 80 was adjusted so that the permeate product in conduit 96 met fiber-grade para-xylene product specifications. At the same time, the membrane area employed in membrane device 20 was adjusted so that the para-xylene recovery for the apparatus was 67 percent. The amount of membrane area in membrane device 50 was chosen to minimize the size and total duty of heat exchangers 40 and 70. The enthalpy of streams in conduits 74 and 42 were adjusted so that the MEI index of the nonpermeate product in conduit 22 was 1. At the same time it was possible to adjust the enthalpy of feed in conduit 14 so that it was not necessary to employ cooler 10.

Results shown in Table IV indicate that it was indeed possible to produce a para-xylene product that contained 99.8 percent para-xylene and simultaneously recover 67 percent of the para-xylene using the process shown in the drawing. This is the first known example of any membrane process that matches the performance requirements of fiber-grade para-xylene purification technologies.

TABLE IV

Results for Process Using Mixed Xylene Feed and para-Xylene Selectivity of 15

| Permeate Pdt 96 PX Content (percent by weight) | PX Recovery (percent by weight) | Membrane Area ($\times 10^{-3}$ ft$^2$) | | |
|---|---|---|---|---|
| | | Module 20 | Module 50 | Module 80 |
| 99.8 | 67 | 1580 | 485 | 121 |

Example 5

Calculations were performed for this example to document the process shown in the drawing which achieved a para-xylene recovery of 75 percent while simultaneously producing a permeate product in conduit 96 that met the fiber-grade purity specification of 99.8 percent para-xylene.

Fresh mixed xylene feed was again introduced only via conduit 14. A para-xylene membrane selectivity of 15 and para-xylene permeability of 0.5 Barrer was employed in each membrane module. The amount of membrane area in device 80 was adjusted so that the permeate product in conduit 96 met the fiber-grade para-xylene product specifications. At the same time, the membrane area employed in membrane module 20 was adjusted so that the para-xylene recovery for the apparatus was 75 percent. The amount of membrane area in membrane device 50 was chosen to minimize the size and total duty of heat exchangers 40 and 70. The enthalpy of streams in conduits 74 and 42 were adjusted so that the MEI index of the nonpermeate product in conduit 22 was 1. At the same time it was possible to adjust the enthalpy of feed from source 12 so that it was not necessary to employ cooler 10.

The simulation results shown in Table V indicated that it was indeed possible to produce a para-xylene product that contained 99.8 percent para-xylene and simultaneously recover 75 percent of the para-xylene using the process according to this invention as depicted in the drawing. This is the first known example of a membrane process that exceeds the performance requirements of conventional para-xylene purification technologies. The impact of increasing the para-xylene recovery while simultaneously meeting the para-xylene purity requirements is expected to be tremendous. This technology could be used to "debottleneck" existing plants, thereby lowering the cost of production, or to lower the capital requirements of building a new para-xylene plant thereby reducing the relative size and cost of the related reaction and fractionation sections. The results shown in Table V show that a little more membrane area was required to meet these more stringent specifications.

TABLE V

| Process Using Mixed Xylene Feed and para-Xylene Selectivity of 15 | | | | |
|---|---|---|---|---|
| Permeate Pdt 96 PX Content (percent by weight) | PX Recovery (percent by weight) | Membrane Area ($\times 10^{-3}$ ft$^2$) | | |
| | | Module 20 | Module 50 | Module 80 |
| 99.8 | 75 | 2420 | 605 | 157 |

Example 6

Calculations were performed for this example using a para-xylene Selectivity of 10 and a para-xylene Permeability of 0.4 Barrer to illustrate the impact of lower membrane selectivity on the performance of the apparatus shown in the drawing. The amount of membrane area in device 80 was adjusted so that the permeate product in conduit 96 met fiber-grade para-xylene product specifications. At the same time, the membrane area employed in membrane device 20 was adjusted so that the para-xylene recovery for the apparatus was 67 percent. The amount of membrane area in membrane device 50 was chosen to minimize the size and total duty of heat exchangers 40 and 70. The enthalpy of streams in conduits 74 and 42 were adjusted so that the MEI index of the nonpermeate product in conduit 22 was 1. At the same time it was possible to adjust the enthalpy of feed from source 12 so that it was not necessary to employ cooler 10.

Results shown in Table VI demonstrate that it was indeed possible to produce para-xylene product that contained 99.8 percent para-xylene and simultaneously recover 67 percent of the para-xylene using the process of this invention as depicted in the drawing when the para-xylene selectivity was 10.

TABLE VI

| Process Using Mixed Xylene Feed and para-Xylene Selectivity of 10 | | | | |
|---|---|---|---|---|
| Permeate Pdt 96 PX Content (percent by weight) | PX Recovery (percent by weight) | Membrane Area ($\times 10^{-3}$ ft$^2$) | | |
| | | Module 20 | Module 50 | Module 80 |
| 99.8 | 67 | 3620 | 966 | 241 |

From the above examples, it is obvious to those skilled in the art that there are many processes where combination of polymer membranes can be used to make an effective para-xylene process. The example below is an illustration of combining a membrane selective for para-xylene and ethylbenzene and a membrane selective for ethylbenzene. The para-xylene and ethylbenzene membrane is one that separates on the basis of size, while the ethylbenzene selective membrane separates on the basis of solubility. These two membranes can be used separately or combined into a single membrane module. While is shown in the figure as being treated separately, this stream could also be recycled to the isomerization reactor where ethylbenzene conversion and isomerization are accomplished in the same reactor.

For the purposes of the present invention, the term "noncondensable" is defined as a gas from chemical or petroleum processing units that is not easily condensed by cooling, for example, nitrogen, carbon dioxide, oxygen, and mixtures consisting mostly thereof.

For the purposes of the present invention, the term "condensable" is defined as gases or vapors which when subjected to appropriately altered conditions of temperature and/or pressure become liquids.

For the purposes of the present invention, the term "membrane separation module" is defined as a plurality of permselective membranes, disposed to form a membrane device.

For the purposes of the present invention, "predominantly" is defined as more than about fifty percent. "Substantially" is defined as occurring with sufficient frequency or being present in such proportions as to measurably affect macroscopic properties of an associated compound or system. Where the frequency or proportion for such impact is not clear substantially is to be regarded as about twenty percent or more.

The term "Essentially" is defined as absolutely except that small variations which have no more than a negligible effect on macroscopic qualities and final outcome are permitted, typically up to about one percent.

Examples have been presented and hypotheses advanced herein in order to better communicate certain facets of the invention. The scope of the invention is determined solely by the scope of the appended claims.

That which is claimed is:

1. A process using perm-selective membranes for simultaneous recovery of a permeate product and a desired non-permeate product from a fluid mixture of compounds, which process comprises:

(1-a) providing a feedstream comprising a mixture of two or more compounds which when subjected to appropriately altered conditions of temperature and/or pressure exhibit a bubble point;

(1-b) providing apparatus comprising means for controlling enthalpy of selected fluids within the apparatus and one or more membrane modules each including first and second zones separated by a solid perm-selective membrane which under a suitable differential of a driving force exhibits a permeability of at least 0.1 Barrer for one of the compounds of the feedstock, each first zone having at least one inlet and outlet for flow of fluid in contact with the membrane, and contiguous with the opposite side thereof a second zone having at least one outlet for flow of permeate;

(1-c) introducing the feedstream into the first zone of one or more of the modules under conditions suitable for permeation, and thereby obtaining permeate and non-permeate streams from the modules; and (1-d) controlling enthalpy to maintain the Membrane Efficiency Index of the non-permeate fluid within a range from about 0.5 to about 1.5.

2. The process according to claim 1 wherein the feedstream comprises a mixture of liquid and condensable vapor.

3. The process according to claim 1 wherein the feedstream comprises a mixture of organic compounds.

4. The process according to claim 3 wherein the mixture of organic compounds includes at least one isomer of an aromatic compound.

5. The process according to claim 3 wherein the mixture of organic compounds includes at least one isomer of xylene.

6. The process according to claim 5 wherein the mixture of organic compounds includes ethylbenzene.

7. A process using perm-selective membranes in multiple groups for simultaneous recovery of desired non-permeate product and purified permeate product from fluid mixtures, which process comprises:

(7-a) providing a feedstream comprising a mixture of two or more compounds which when subjected to appropriately altered conditions of temperature and/or pressure exhibit a bubble point;

(7-b) providing apparatus comprising means for controlling enthalpy of selected fluids within the apparatus and a plurality of membrane modules disposed in a first product group, a second product group, and at least one intermediate group, each module including first and second zones separated by a solid perm-selective membrane which under a suitable differential of a driving force exhibits a permeability of at least 0.1 Barrer for one of the compounds of the feedstock, each first zone having at least one inlet and outlet for flow of fluid in contact with the membrane, and contiguous with the opposite side thereof a second zone having at least one outlet for flow of permeate;

(7-c) introducing the feedstream into the first zone of one or more of the first product modules under conditions suitable for permeation, and thereby obtaining permeate and non-permeate product streams from the first product modules;

(7-d) distributing the permeate from the first product modules into the first zone of one or more of the intermediate modules under conditions suitable for permeation, and thereby obtaining permeate and non-permeate streams from the intermediate modules;

(7-e) returning at least a portion of the non-permeate from the intermediate modules into the first zone of one or more of the first product modules under conditions suitable for permeation;

(7-f) distributing the permeate from the second zones of the intermediate group of modules into the first zones of the second product group modules under conditions suitable for permeation, thereby obtaining non-permeate streams and final permeate product streams from the second product modules;

(7-g) returning at least a portion of the non-permeate from the second product modules into the first zone of one or more of the intermediate modules under conditions suitable for permeation; and (7-h) controlling enthalpy to maintain the Membrane Efficiency Index of at least one non-permeate fluid within a range from about 0.5 to about 1.5.

8. The process according to claim 7 wherein the feedstream comprises a mixture of liquid and condensable vapor.

9. The process according to claim 7 wherein the feedstream comprises a mixture of organic compounds.

10. The process according to claim 9 wherein the mixture of organic compounds includes at least one isomer of an aromatic compound.

11. The process according to claim 9 wherein the mixture of organic compounds includes at least one isomer of xylene.

12. The process according to claim 11 wherein the mixture of organic compounds includes ethylbenzene.

13. The process according to claim 7 wherein the Membrane Efficiency Index of the non-permeate fluid from the second product modules is maintained within a range from about 0.5 to about 1.5.

14. The process according to claim 13 wherein the feedstream comprises a mixture of organic compounds that includes at least one isomer of xylene.

15. The process according to claim 14 wherein the mixture of organic compounds includes ethylbenzene.

16. The process according to claim 13 wherein the Membrane Efficiency Index of the non-permeate fluid from the first product modules is maintained within a range from about 0.5 to about 1.5.

17. The process according to claim 16 wherein the feedstream comprises a mixture of organic compounds that includes at least one isomer of xylene.

18. The process according to claim 17 wherein the mixture of organic compounds includes ethylbenzene.

19. The process according to claim 18 wherein the Membrane Efficiency Index of the non-permeate fluid from the intermediate modules is maintained within a range from about 0.5 to about 1.5.

20. A separation apparatus using perm-selective membranes in multiple groups for simultaneous recovery of desired non-permeate product and purified permeate product from fluid mixtures, which apparatus comprises:

a plurality of membrane modules disposed in a first product group, a second product group; and at least one intermediate group, each module including first and second zones separated by a solid perm-selective membrane which under a suitable differential of a driving force exhibits a permeability of at least 0.1 Barrer for one of the compounds of the feedstock, each first zone having at least one inlet and outlet for flow of fluid in contact with the membrane, and contiguous with the opposite side thereof a second zone having at least one outlet for flow of permeate;

means for distributing permeate from the first product modules into the first zone of one or more of the intermediate modules under conditions suitable for permeation, and returning non-permeate streams from the intermediate modules to inlets of the first product modules;

means for distributing permeate from the intermediate modules into the first zone of one or more of the second product modules under conditions suitable for permeation, and returning non-permeate streams from the second product modules to inlets of the intermediate modules; and means for controlling enthalpy of selected fluids within the apparatus to maintain the Membrane Efficiency Index of at least one non-permeate fluid within a range from about 0.5 to about 1.5.

* * * * *